(12) United States Patent
Bove

(10) Patent No.: US 7,427,730 B2
(45) Date of Patent: Sep. 23, 2008

(54) SOUND WAVE THERAPY APPLICATION SYSTEM

(76) Inventor: Thomas Bove, 3709 S. Conklin Rd., Greenacres, WA (US) 99016

( * ) Notice: Subject to any disclaimer, the term of this patent is extended or adjusted under 35 U.S.C. 154(b) by 679 days.

(21) Appl. No.: 11/031,987

(22) Filed: Jan. 6, 2005

(65) Prior Publication Data
US 2006/0173323 A1 Aug. 3, 2006

(51) Int. Cl.
H05B 6/70 (2006.01)
A61B 8/00 (2006.01)

(52) U.S. Cl. ............................ 219/691; 600/439

(58) Field of Classification Search ............ 219/691, 219/678, 692, 693, 690, 696; 600/407, 410, 600/411, 439
See application file for complete search history.

(56) References Cited

U.S. PATENT DOCUMENTS

| 5,277,692 | A | 1/1994 | Ardizzone |
| 5,514,072 | A | 5/1996 | Ardizzone |
| 5,538,495 | A | 7/1996 | Ardizzone |
| 5,871,438 | A | 2/1999 | Ardizzone |
| 6,065,210 | A | 5/2000 | Bove |
| 6,275,340 | B1 * | 8/2001 | Brown ................ 359/630 |
| 6,322,491 | B1 | 11/2001 | Bove et al. |
| 6,328,684 | B1 | 12/2001 | Ardizzone |
| 6,535,754 | B2 * | 3/2003 | Fishbein et al. ......... 600/422 |
| 6,626,820 | B1 | 9/2003 | Ardizzone |
| 6,692,427 | B2 | 2/2004 | Bove et al. |
| 6,846,379 | B1 | 1/2005 | Bove et al. |
| 2002/0188323 | A1 * | 12/2002 | Penner et al. ............ 607/2 |
| 2007/0010702 | A1 * | 1/2007 | Wang et al. ............. 600/8 |

* cited by examiner

Primary Examiner—Daniel L Robinson
(74) Attorney, Agent, or Firm—Wells St. John PS

(57) ABSTRACT

A system including a method and apparatus for applying sound wave therapy to a mammal utilizing a silicone layer at or near the skin to enhance the therapeutic affect.

14 Claims, 9 Drawing Sheets

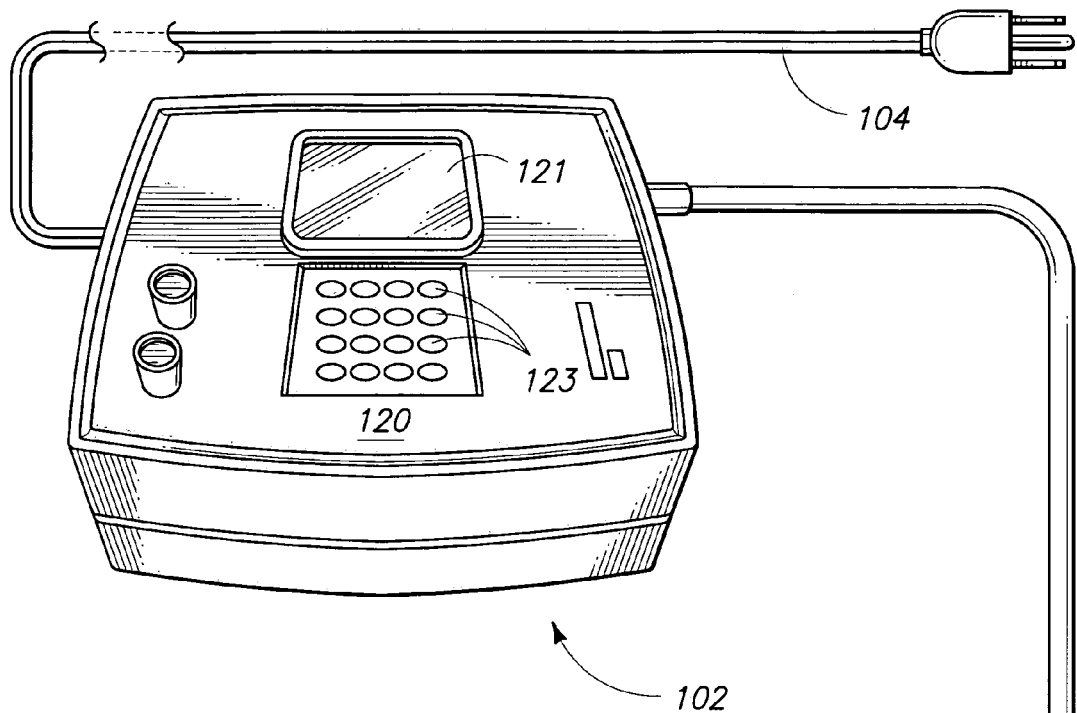
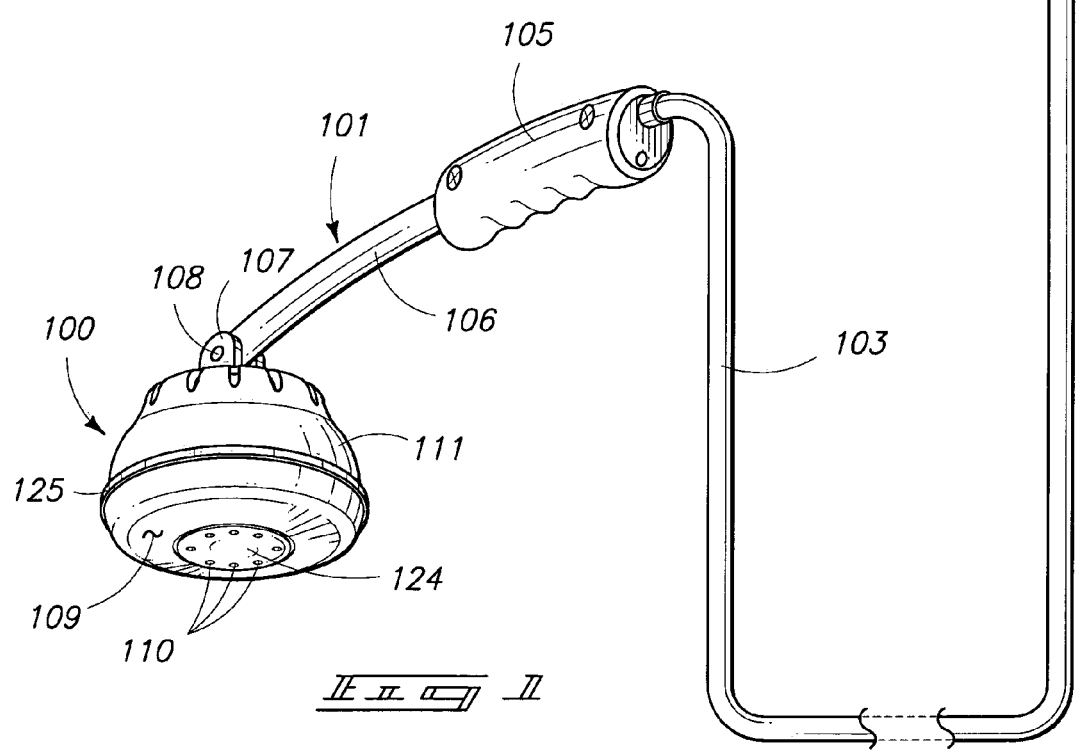
FIG. 1

4 SEGMENTS

9 SEGMENTS

30 SEGMENTS 30,000 SEGMENTS

SOUND WAVE THERAPY APPLICATION SYSTEM

TECHNICAL FIELD

This invention pertains to a sound wave therapy application system, more particularly a sound or vibration wave therapy application system which utilizes a layer of silicone for placement between the sound wave generator and the skin to which the sound waves are to be applied.

BACKGROUND OF THE INVENTION

Sound wave therapy has been known for many years for its positive effect on humans and animals such as horses, and in a variety of applications.

In certain medical and therapy applications, silicone sheets have been utilized for many different applications, one of which is for the management of hypertrophic and keloid scarring. While there is scientific debate as to the specific reasons a silicone sheet or silicone layer are effective, there are cases which affirm the efficacy of the silicone for some of these applications. While some believe the silicone creates, generates or facilitates a static electricity or electrical field, the specific reason or therapeutic affect on the skin is not as important as the results being obtained.

It is therefore an object of some embodiments of this invention to provide an improved application system for the application of waves for a therapeutic affect.

Other objects, features, and advantages of this invention will appear from the specification, claims, and accompanying drawings which form a part hereof. In carrying out the objects of this invention, it is to be understood that its essential features are susceptible to change in design and structural arrangement, with only one practical, and preferred embodiment being illustrated in the accompanying drawings, as required.

BRIEF DESCRIPTION OF THE DRAWINGS

Preferred embodiments of the invention are described below with reference to the following accompanying drawings.

FIG. 1 is an example of one embodiment of a wave applicator contemplated by this invention, shown with a wave generator;

DETAILED DESCRIPTION OF THE PREFERRED EMBODIMENTS

Figure 2:
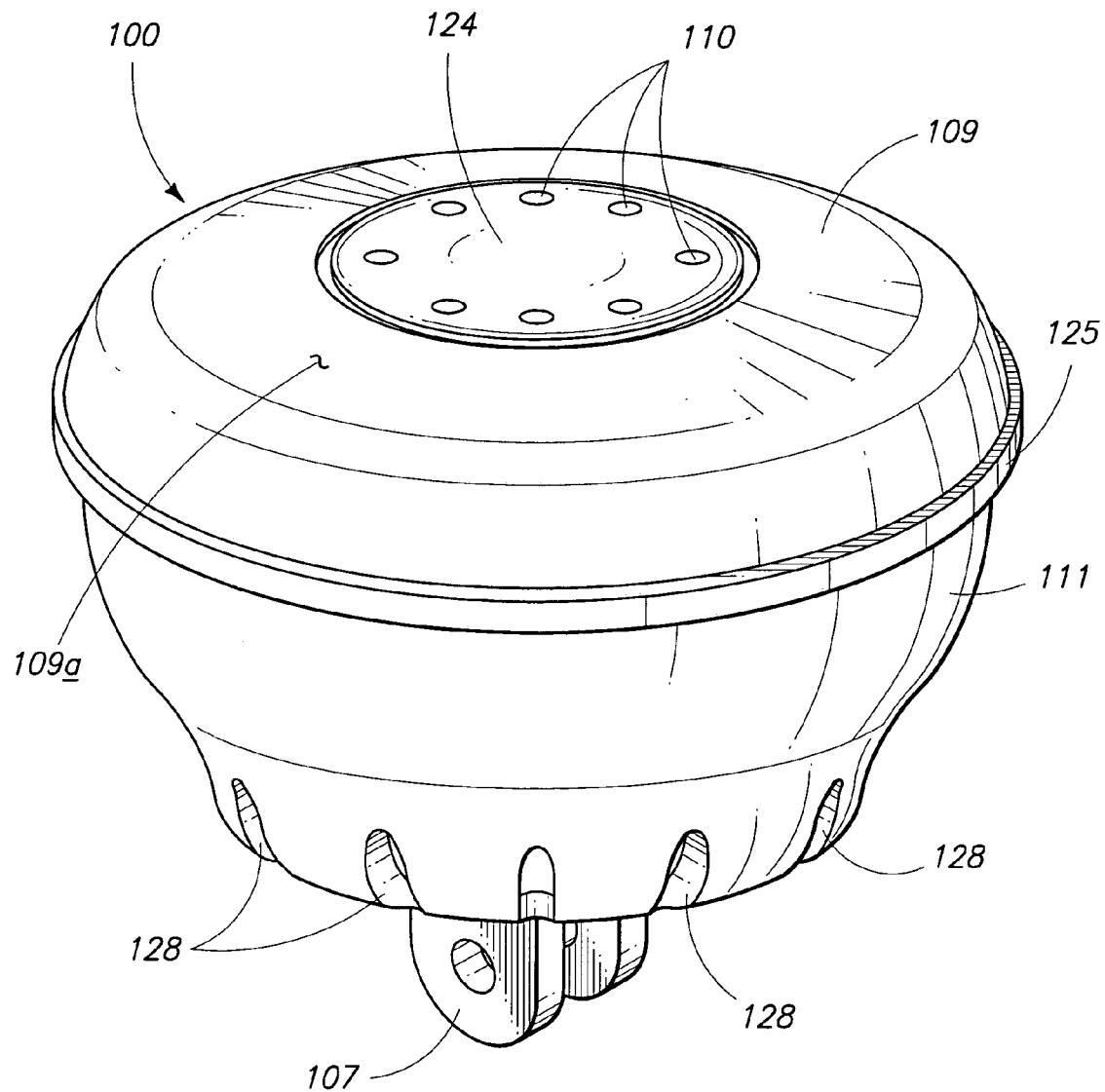
FIG. 2 is a front perspective view of one embodiment of a wave applicator, which may be contemplated by this invention.

Fasteners, materials, drive mechanisms, control circuitry, manufacturing and other means and components utilized to make and implement this invention are known and used in the field of the invention described, and their exact nature or type is not necessary for an understanding and use of the invention by a person skilled in the art or science; therefore, they will not be discussed in significant detail. Furthermore, the various components shown or described herein for any specific application of this invention can be varied or altered as anticipated by this invention and the practice of a specific application or embodiment of any element may already be widely known or used in the art or by persons skilled in the art or science; therefore, each will not be discussed in significant detail.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

The terms "magnet" and "magnetic material" may include any type or kind of magnet or magnetic material with no one in particular being required to practice this invention. By way of providing some, but not an exhaustive list of examples, this may include without limitation, permanent magnets, magnetic materials which create a changing magnetic field, ferromagnetic components, and others. The magnets or magnetic material may be fluxing, fixed, moving or otherwise, within the contemplation of this invention, and may create pulsed, changing, fluxing, modulating, and/or fixed/constant magnetic, waved or energy fields (as a few examples) within the contemplation of this invention. They may including alternating poles, north poles, south poles, or combinations thereof, and different shapes of the magnets and magnetic fields, all within the same magnet or magnetic layer, within the contemplation of this invention.

It will be appreciated by those of ordinary skill in the art that a device and method such as this, for the application of waves for various treatments can be used in any one of a number of different ways, with no one in particular being required to practice this invention. For instance, this invention may be used or attempted in the treatment of scar tissue, inflamation and the reduction of pain, as some of the possible examples of uses or embodiments for applications.

One of the components of this invention is a layer of silicone or a silicone module. Silicone is generally any one of various polymeric organic silicon compounds such as oils, greases, or plastics and used for water resistant and heat resistant lubrications, varnishes, binders, and as electric insulators. Silicone may come in many different forms, such as a rubber form made from silicon elastomers, which may be noted for its retention of flexibility, resilience and tensile strength over a wide temperature range.

In this case, a silicone layer or module, depending on the application, is designed to mechanically or operatively connect to a coil that can pulsate at any one of a number of different frequencies, or to vibrate or pulsate at multiple frequencies concurrently within the coil. The electrical coil is generally suspended and surrounded by a magnet or what may be also referred to as a permanent magnet, because it is generally preferred to fix the permanent magnet relative to a framework of the applicator.

Although a coil is generally a series of loops or a number of turns of wire, especially in a spiral form, for electromagnetic affect or for providing electrical resistance, it will be appreciated by those of ordinary skill in the art that other devices may be utilized which are technically not coils within the contemplation of this invention. Although the coil may be the preferred way to provide the recipient of waves and to initiate vibration, there may be any one of a number of other devices which may be similarly used, although a wire coil is the preferred device. The coil may be suspended by any one of a number of different means, and then surrounded by a permanent magnet.

Generally as the coil receives sine wave frequencies through the windings, it causes pulsations to occur and the silicone module moves with the coil pulsations. The silicone module system may be configured to receive any shape and number of magnets by creating pockets within the geometry of the module or framework. The coil may receive sine wave frequencies from any one of a number of different sources or wave generators, such as a high speed microprocessor in some embodiments contemplated by this invention. The high speed microprocessor may be utilized to generate and transmit to the coil different digital, analog and sinusoidal frequencies or waves.

In this case, a preferred frequency is created within the microprocessor at a minimum rate of thirty thousand (30,000) line segments per sine wave by imparting them on a microprocessor, which then creates the sine waves as shown in FIG. 13. A digital signal from the microprocessor is then fed into a digital-to-analog converter, and the output of the digital-to-analog converter is connected to an amplifier. The amplitude of the amplifier may be fully adjustable through variable resistence mechanisms.

An interval circuit may also be in series with the output of the amplifier to control a time delay between pulses, or between frequencies or waves being transmitted.

It is a mechanical linkage or positional relationship between the silicone layer and the frequency driven coil that creates some of the benefits, which are believed to result from the use of the invention. The invention also has applications relating to methods utilizing silicone in conjunction with static magnets, which are connected to, mounted to or positioned relative to the applicator framework.

In past studies, experiments and uses of patches of silicone, the treatment of scar tissue has been accomplished over various areas. There have been numerous scientific studies regarding the efficacy of silicone sheets on scar tissue, and some of the scientific studies suggest that silicone works by forming a static electrical field between the silicone sheet and the skin of the person to whom the applicator is being applied. In the case of scar tissue, smoothing and flattening affect has been shown to occur with an increase in blood circulation to produce an improved skin tone.

Other studies also suggest that static magnets can alter the behavior of nerve tissues, such as by the reduction of chronic pain sensations. It has been theorized that magnetism can suppress the actual potential firings of nerve impulses in humans, and thereby control or suppress pain and other effects of nerve impulses. Some of the studies referred to, test electromagnetic fields in and around the skin, and have indicated that the electromagnetism may also relieve pain by selectively increasing the excitability of large nerve fibers within the body, which then may block the pain gate for pain to be transmitted through nerves to the brain.

It will also be appreciated by those of ordinary skill in the art that the invention incorporates a silicone module containing pockets that can receive any shape, number and style of static magnets. The silicone module is designed to pulsate at any desired frequency or combination of frequencies. When the static magnets move, static magnetic fields simulate an electromagnetic field. The electromagnetism is defined as a magnetic field that is coupled onto electrosine wave paths. Embodiments of this invention utilize the mechanical pulsations of static magnets to achieve an infinitely adjustable pulsing magnetic field.

As stated above, silicone is one of the best known conductors of static electricity and in aspects of this invention, as the silicone module pulsates, an increase in static impulses is established. Many scientists have theorized that static electricity has a beneficial and profound healing affect on the human body.

Aspects of this invention further include a combination of a silicone layer for direct or near application to the skin, magnetism and a frequency which is imparted on the coil to develop and treat scar tissue, pain, inflamation, discomfort and skin tone related issues.

It will also be appreciated by those of ordinary skill in the art that as sinusoidal wave pulsations are energized into the coil windings, the silicone module pulsates with the coil pulsations due to the relative position or location of the respective components.

In a preferred configuration, the aspects of the invention may be linked to or even incorporate a control unit that includes a programmable logic controller (PLC), a high speed microprocessor (HSMP), a digital-to-analog converter (DAC) and amplifier circuitry to provide the one or more waves which are pulsed or energized into the coil in the applicator. The control unit provides, selects and controls any desired frequency or set of frequencies that are applied or energized to the coil windings.

A microprocessor with memory storage is also utilized to create multiple sine wave frequencies into one output. In certain embodiments or aspects of this invention, the memory storage may be used such that a combination of frequencies can be placed into one input and the particular frequencies or wave pattern of any one frequency within the combination can be altered as desired.

The pulsations of the silicone module or applicator can be any one of a number of different pulsation rates from, for example, twenty (20) waves per second to twenty thousand (20,000) waves per second or hertz. It will also be appreciated by those of ordinary skill in the art that as the multiple frequencies are mixed into one output, the amount of resistance or friction is increased, which causes both rapid and slower pulses within the same wavelength. The exchange between both negative and positive electrons along the surface body of atoms is also increased during a particular wavelength.

Sine waves may be achieved with a microprocessor that has a speed of approximately fifty (50) megahertz, although no one in particular is required to practice this invention. The microprocessor speed effects the amount of digital segments that can be generated over the imposed sine wave. The microprocessor generates a wave of closely knitted segments to create the perfect sine wave with no distortion. The digital sine wave is then connected into a digital-to-analog converter. The digital to analog converter takes the signal from the microprocessor and makes it amplifiable.

The term "therapeutic" is also used herein to cover and include any such wave or energy source which has a therapeutic, health care or biological affect on a recipient, including a magnetic field, a static field, an electric field, infrared waves or any others with a therapeutic or health care affect. For example, it may later be determined that wave forms or energy anywhere in the electromagnetic spectrum or sound wave spectrum provide a therapeutic or health care affect to the recipient. Both are intended to be included herein.

Silicone rubber is a unique synthetic elastomer made from cross-linked polymer, which is reinforced with silica. The characteristics of silicone rubber are such that it provides a balance of mechanical and chemical properties required in many applications. Silicone rubber generally has temperature stability, inertness, translucent, chemical resistence, sealing performance, and possesses electrical properties, such as insulating qualities. Silicone is nonconductive, because of the chemical nature and, when compounded with proper fillers and additives, are used to produce rubber for a wide range of electrical insulating applications. When the term "silicone" is used herein, it refers not only to silicone, but to other forms and derivatives of silicone, such as fluorosilicone.

The microprocessor generates waves, which may be sound waves or electrical waves, such as electrical signals. The at least semi-flexible silicone interface is moved or vibrated by sound waves created by the coil and magnet combination in the wave applicator.

The electromagnet or coil is positioned in a constant magnetic field, generally created by a permanent magnet, as shown. The two (2) magnets, the electromagnet or coil and the permanent magnet, interact with each other as magnets typically do. The positive end of the electromagnet or coil is attracted to the negative pull of the permanent magnetic field, and the negative pull of the electromagnet is repelled by the permanent magnets negative pull. When the electromagnets pull or orientation switches, so does the direction of repulsion and attraction. In this way, the alternating current constantly reverses the magnetic forces between the coil and the permanent magnet, and this pushes the coil back and forth rapidly like a piston, causing vibrations in the air. When the electrical current flowing through the coil changes direction, as it does with alternating current, the coils polar orientation reverses and this changes the magnetic forces. When the coil moves, it pushes and pulls the semi-flexible silicone layer, which vibrates the air in front of the configuration, thereby creating the sound waves. The electrical audio signal can also be interpreted as a wave. The frequency and amplitude of the wave dictates the rate and distance that the coil actually moves, which in turn determines the frequency and amplitude of the sound waves produced by the movement.

FIG. 1 illustrates an example of one embodiment of a wave therapy application system, which in this case happens to be a sound wave therapy applicator. The wave therapy applicator 100, is pivotally attached to holding structure 101, which includes handle 105 and bar 106. The wave applicator 100 is pivotally attached about axis 108, which interacts with holding structure attachment 107. Wave conductor 103 operatively connects the wave applicator to a wave generator 102. The wave conductor may be one or more electrical conductors or fiber optic conductors, and said conductors may be routed through the internal cavity in holding structure 101 and handle 105. The wave generator housing 120 may be any one of a number of types of housings, including one of a number of types of controls or displays, such as keypad 123 and display 121. It would be appreciated by those of ordinary skill in the art that the wave generator 102 may be powered by any one of a number of different waves, including through electrical power cord 104 for the receipt of alternating current for the source of power for the wave generator 102.

In looking more particularly at the wave applicator 100, it includes silicone interface 109, magnets 110, pulsating interface 124, which is also preferably made of silicone, and plastic housing 111. Vents 128 are provided in plastic housing 111, and coupler 125 is provided on silicone interface 109 to allow easier coupling to plastic housing 111, as better shown in later drawings.

It will be appreciated by those of ordinary skill in the art that while one example of an embodiment is shown in FIG. 1, there are any one of a number of other combinations which may be utilized to practice this invention. For instance, although a holding structure 101 with a handle 105 is shown, one need not be provided and plastic housing 111 could be reconfigured to allow the direct handling of the wave applicator. It will also be appreciated by those of ordinary skill in the art that any one of a number of types of waves and wave generators may be utilized within the contemplation of this invention, with no one in particular being required to practice the invention.

FIG. 2 is a perspective view of the interface side of wave applicator 100, illustrating plastic housing 111, vents 128, holding structure attachment 107, silicone interface 109, coupler 125, magnets 110 and semi-flexible member 124, which may pulsate in response to waves or sound waves.

It will be appreciated by those of ordinary skill in the art that there are any one of a number of different configurations, looks and interfaces, which may be utilized as part of this invention or to practice this invention, with no one in particular being required. The silicone member has silicone interface surface 109A.

Figure 3:
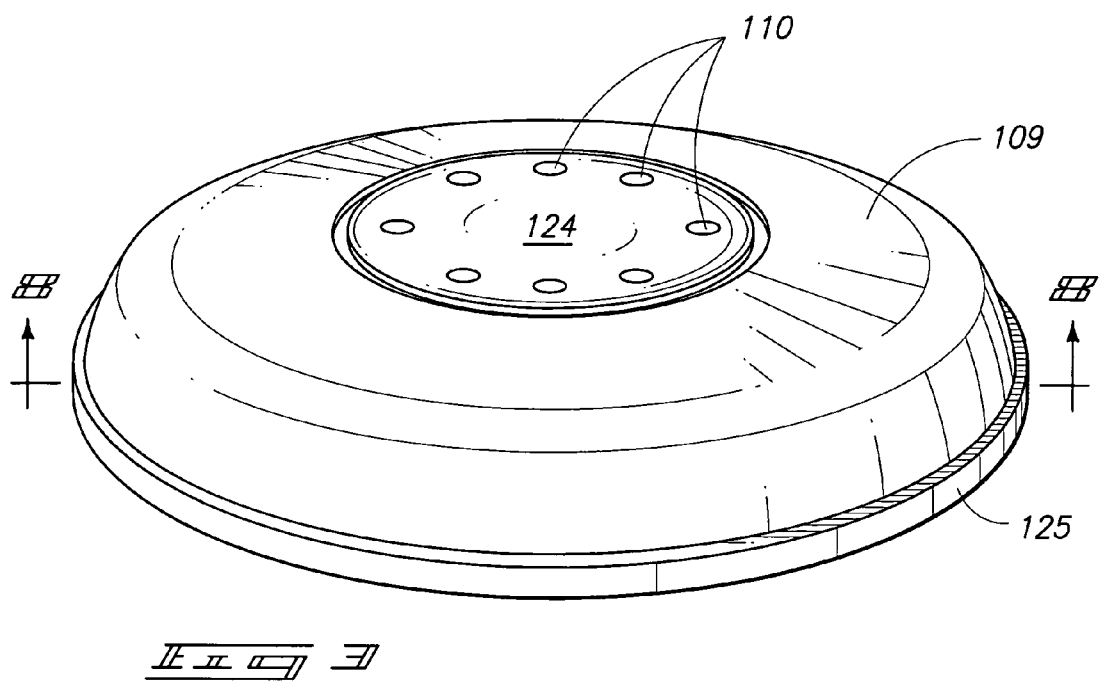
FIG. 3 is a front perspective view of an exemplary silicone interface, which may be utilized as part of the wave applicator illustrated in FIG. 2.

FIG. 3 is a perspective view of silicone interface 109, showing coupler 125, magnets 110 and at least semi-flexible member 124.

Figure 4:
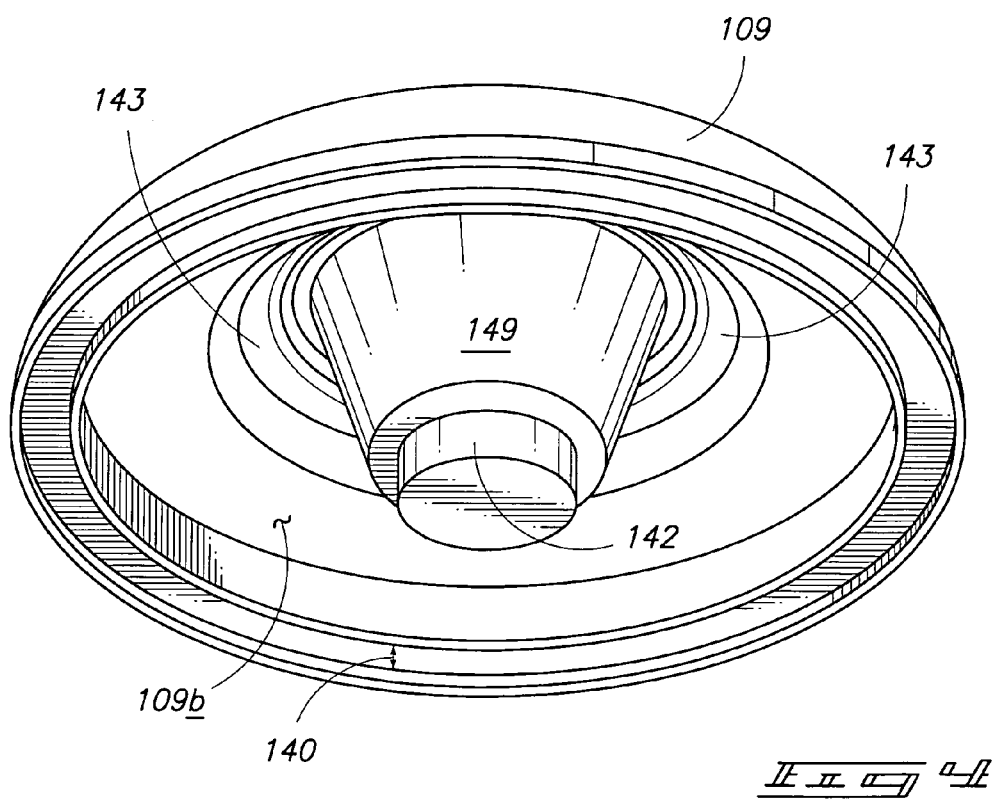
FIG. 4 is a lower front perspective view of the silicone interface illustrated in FIG. 3, showing the underside thereof.

FIG. 4 is a bottom perspective view of the silicone interface layer 109, illustrating internal surface 109b, coil support stub 142, internal support 149 and a relieved bottom section 143 to allow the silicone area to vibrate or pulsate in response to waves. The slot 140 in coupling 125 provides a slot in which the plastic housing may be inserted to hold the assembly together.

Figure 5:
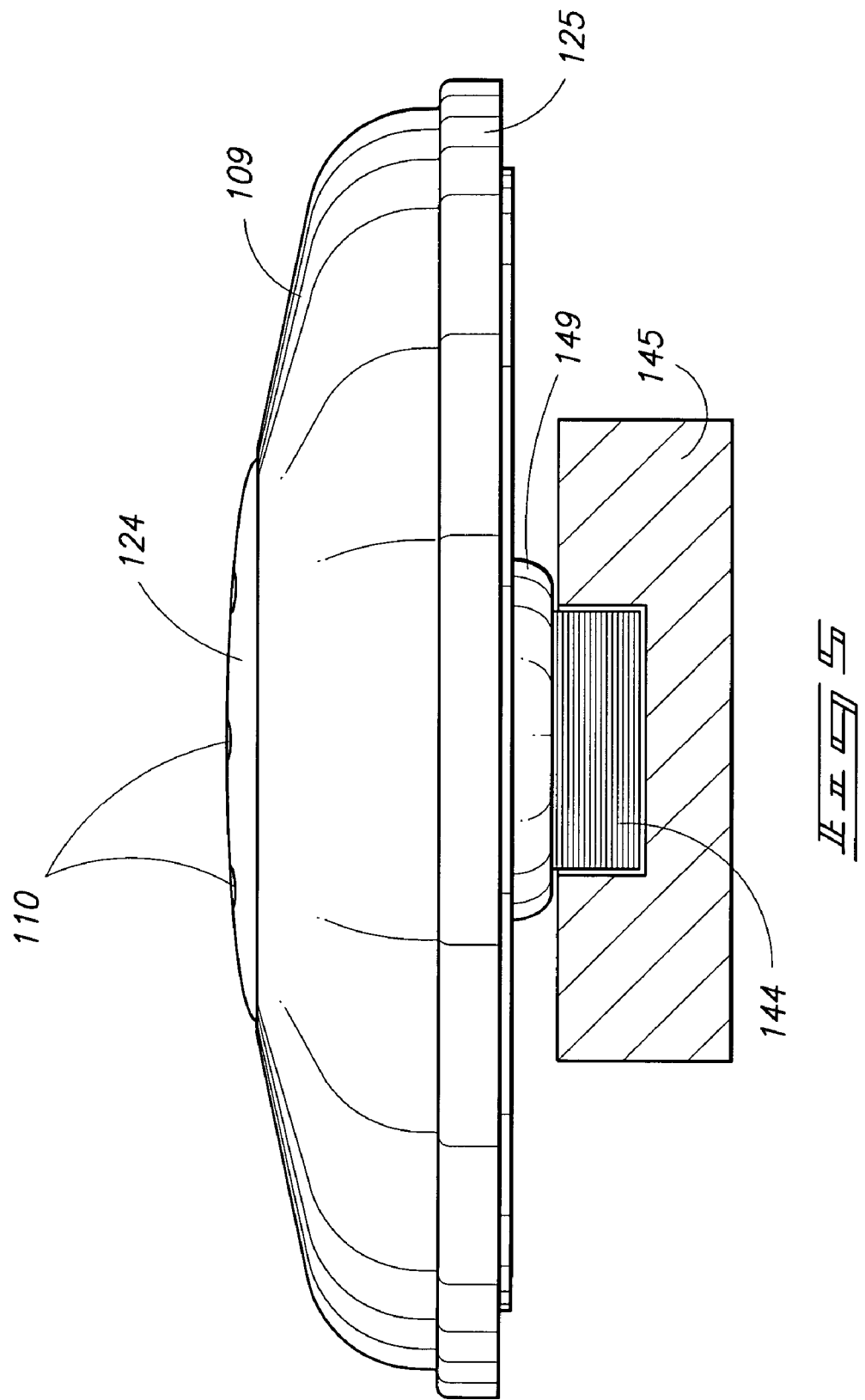
FIG. 5 is a front elevation view of the silicone interface, and a cross-section view of an electrical coil and magnet shown combined with the silicone interface in this figure.

FIG. 5 is a front elevation view of an example of one embodiment of the silicone interface showing a cross-section of a permanent magnet 145 with a coil 144 therein. Silicone interface 109, semi-flexible portion 124, magnets 110 and internal support 149 are also shown in FIG. 5.

Figure 6:
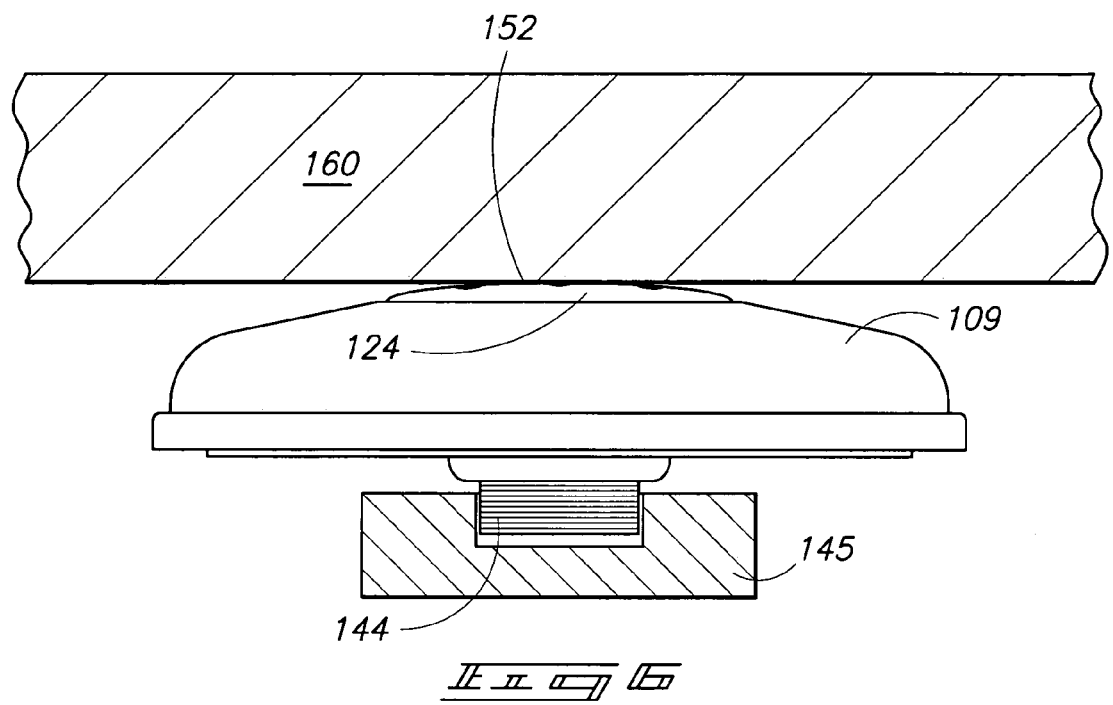
FIG. 6 is a front elevation view of the configuration illustrated in FIG. 5 applied against the target surface, which may be skin.
Figure 7:
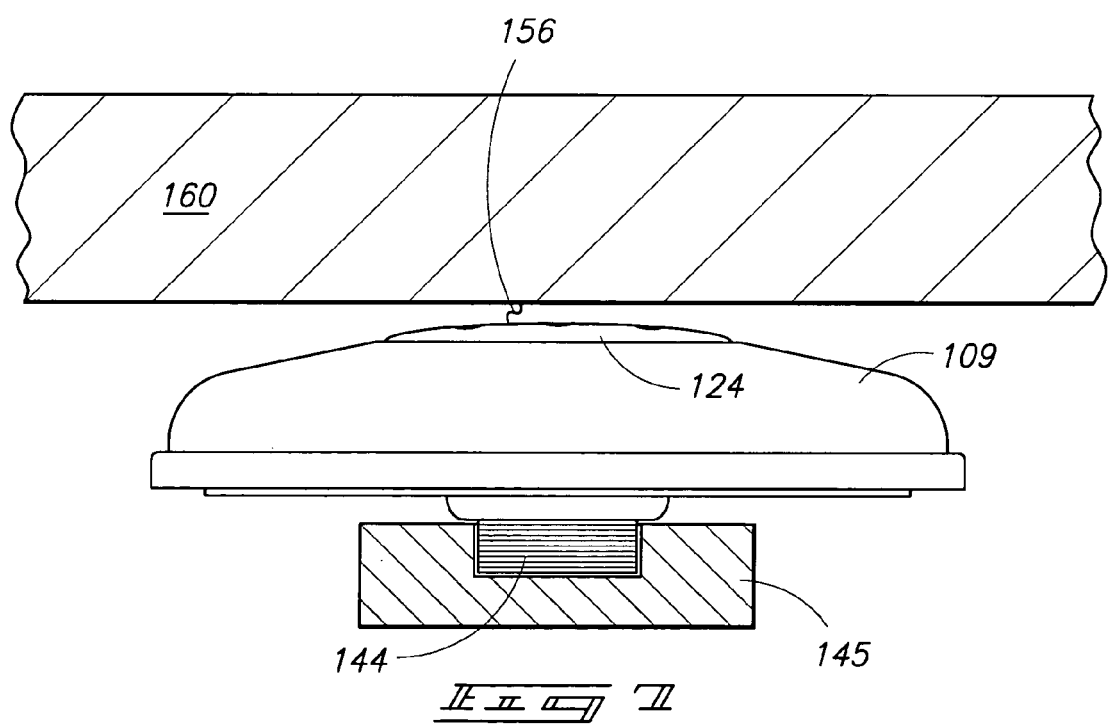
FIG. 7 is the same view as FIG. 6, only showing the movement or pulsing of the silicone interface away from the skin in response to waves.

FIGS. 6 and 7 show a similar view to that shown in FIG. 5, only illustrate the relative movement of a silicone layer or interface relative to skin or the target area 160 to receive the wave therapy. FIG. 6 shows the configuration in contact 152 with the target area 160, and FIG. 7 illustrates it in a receded condition in response to therapeutic waves being received. The gap 156 shown in FIG. 7, is larger than would be experienced for illustration purposes.

The semi-flexible portion 124 of the silicone interface may be pulsated or otherwise vibrated by the wave or combination of waves imparted thereon. The waves are imparted by the application of waves through the coil 144, and the interaction of the coil relative to the permanent magnet 145. The waves or combination of waves imparted cause the relative movement of the coil 144 within the magnet 145. Preferably, the permanent magnet 145 is stationary and by alternating opposing forces for the coil to move relative thereto, in response to therapeutic waves being received into the coil. The static electricity within the silicone is a phenomenon that occurs when friction shows itself as an accumulation of electrons (a negative charge) or loss of electrons (a positive charge) on an atom or the surface of a body of atoms. Since atoms have no charge, but can gain or loose electrons, the pulsating or vibrational movement of the silicone is a unique method for the surface atoms of the skin to gain and loose electrons. In looking at FIGS. 6 and 7, the FIG. 6 would show an accumulation of electrons or negative charge during an upward pulsating or vibrating movement, whereas FIG. 7 would show a gap 156, which represents a loss of electrons (a positive charge) during a downward pulsating or vibrating movement. It is preferable that the permanent magnet 145 completely surround the coil.

Figure 8:
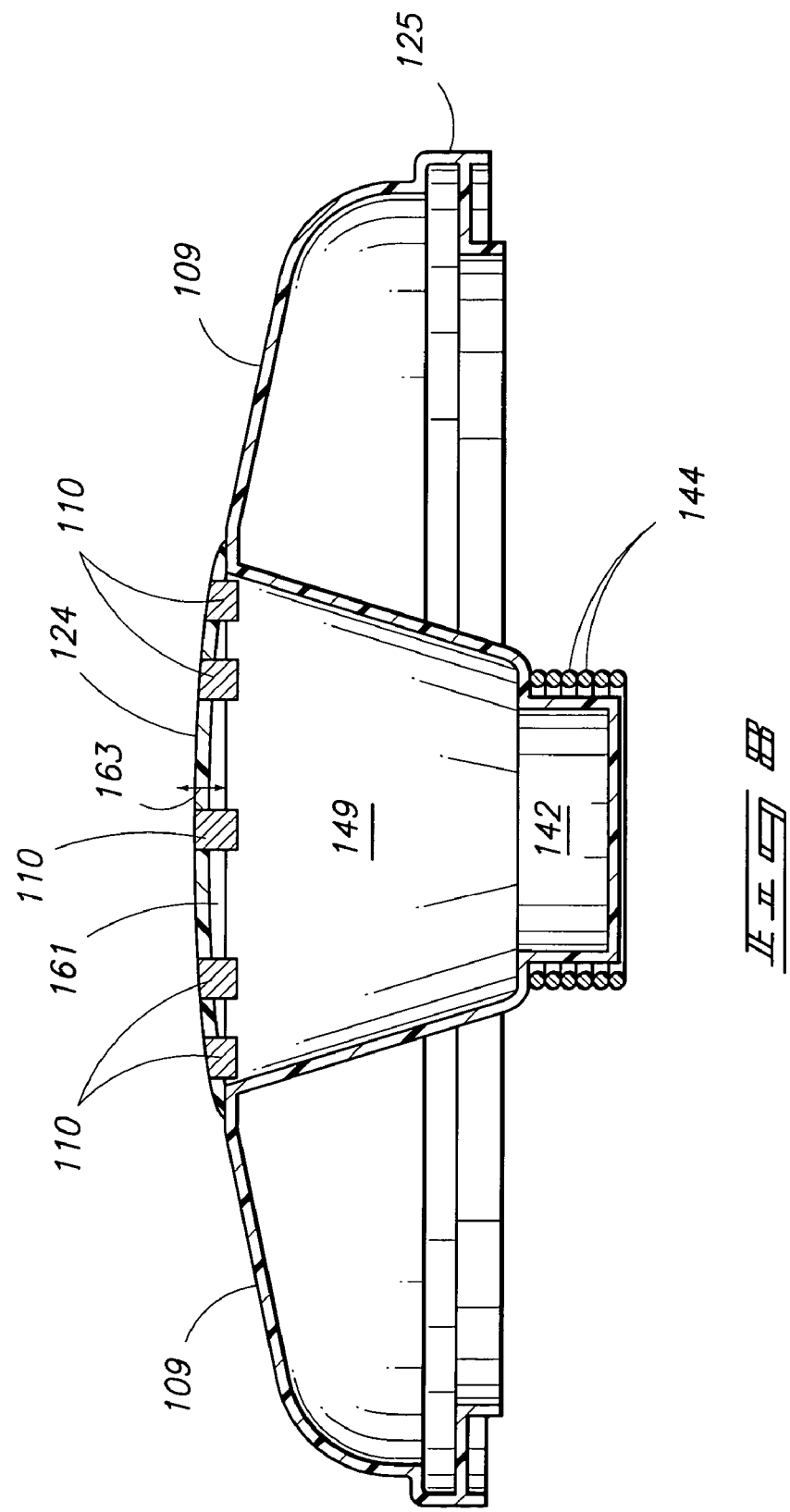
FIG. 8 is a section view of the configuration shown in FIG. 5.

FIG. 8 is a cross-section of the silicone interface 109, shown in prior figures, as well as the coil 144, also shown in other figures. The permanent magnet 145 is not shown in this figure, for illustrative purposes. FIG. 8 illustrates magnets 110, semi-flexible silicone 124, which may also be fully-flexible silicone 124, gap 161, which represents the gap created by the movement of semi-flexible portion 124 relative to internal support 149, as represented by movement arrow 163. Coil stub 142 is shown attached to internal support 149, in providing a stub around which coil windings 144 are wound, and move relative thereto.

In one embodiment of the invention, it is preferable that the waves generated by the coil and movement of the coil, and effect on the air, would cause a relative movement of the semi-flexible portion 124 of silicone interface 109, thereby imparting therapeutic waves on the target, such as skin.

Figure 9:
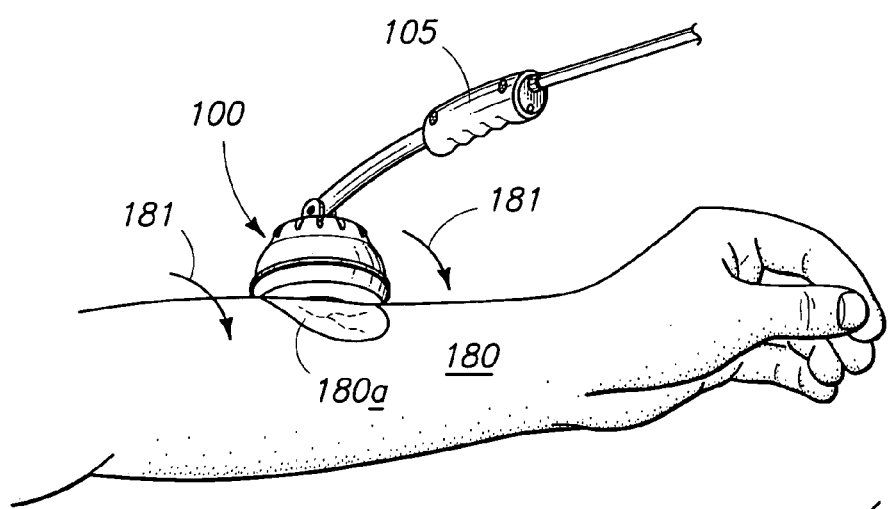
FIG. 9 is an elevation view showing the applicator being placed on target tissue, which may be scar tissue, on a human arm.

FIG. 9 is a perspective view of the applicator 100 with handle 105 being utilized to impart wave therapy on a human arm 180, which includes a target area 180*a*. The handle is utilized to move the applicator in the direction or manner shown by arrows 181 to the target area to receive the therapeutic waves, which may be sound waves.

Figure 10:
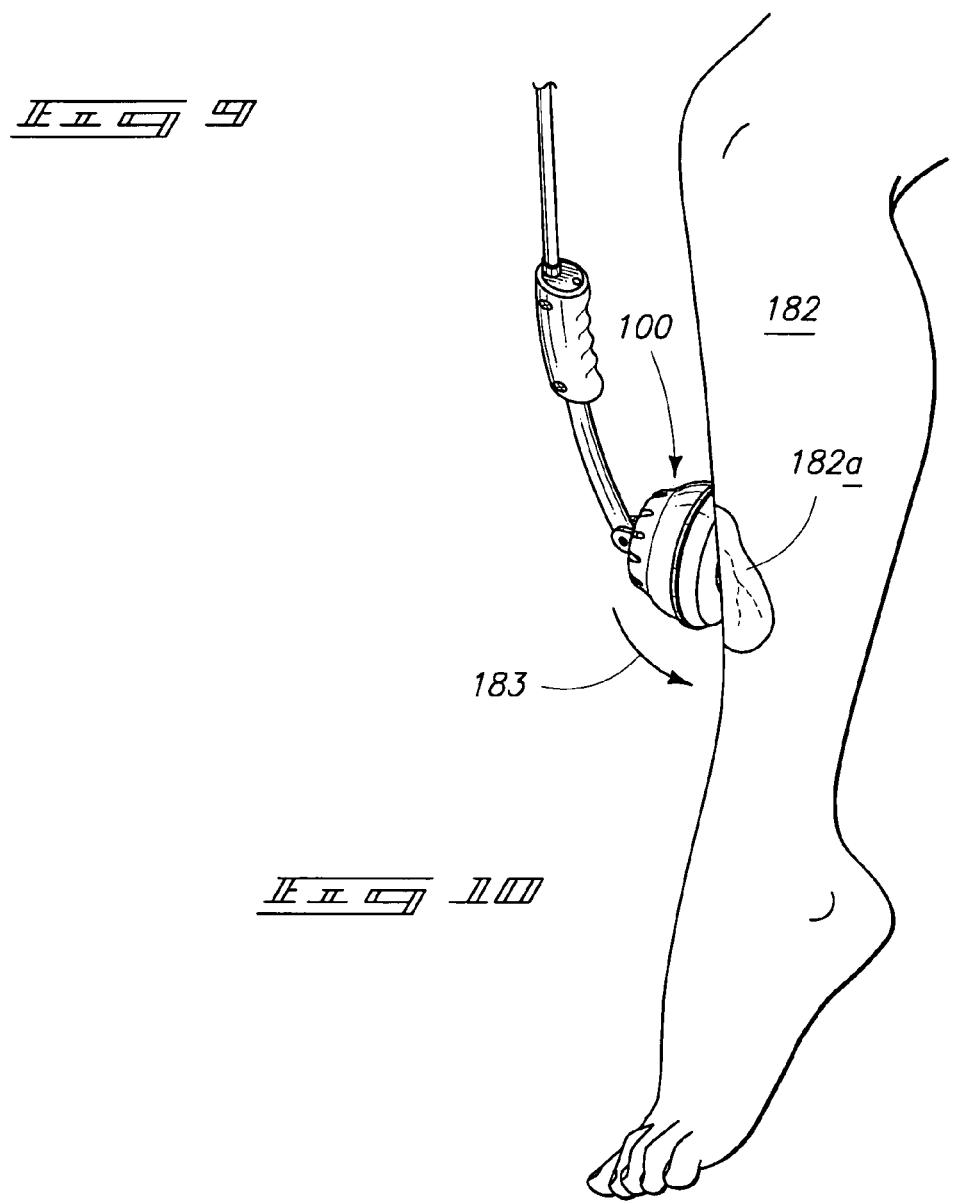
FIG. 10 is an elevation view showing the applicator being placed on target tissue, which may be scar tissue, on a human leg.

FIG. 10 is an elevation view of the applicator 100 being moved in the direction of arrow 183 to apply wave therapy to a human leg 182, at a scar or other target area 182*a*.

Figure 11:
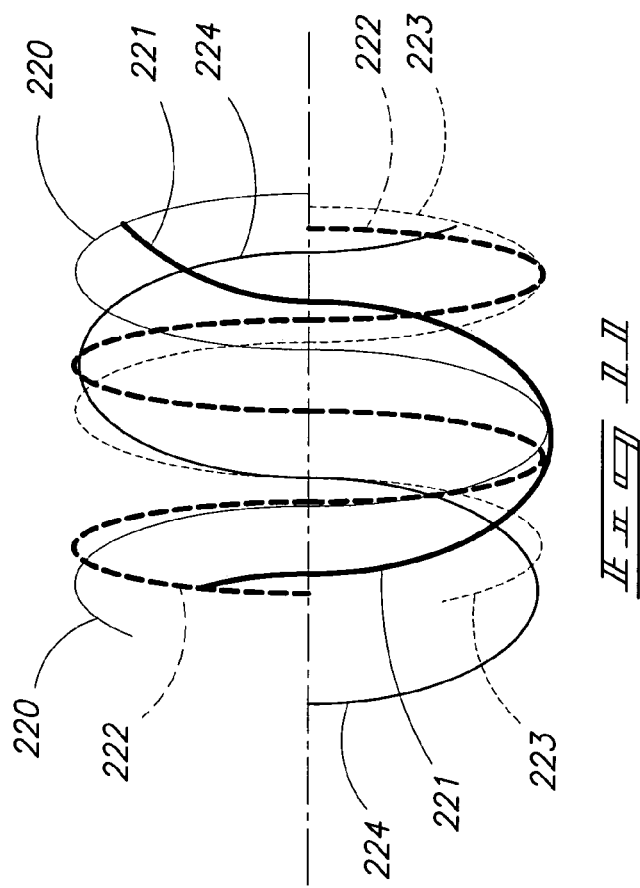
FIG. 11 is a schematic depiction of one example or one embodiment of a combination of waves, which may be applied to the target surface concurrently.

FIG. 11 is a schematic representation of one example of an embodiment which includes a combination of five (5) waves, which are generated by the wave generator and utilized for the application of wave therapy in one embodiment of this invention. FIG. 11 shows a representative first wave 220, a representative second wave 221, a representative third wave 222, a representative fourth wave 223, and a representative fifth wave 224. An exemplary or typical wave formation for any one of the first, second, third, fourth or fifth waves could be 100 hertz, 500 hertz, 1,000 hertz, 5,000 hertz, 10,000 hertz, and 20,000 hertz coupled into one output. Since the control unit is infinitely adjustable, both the practitioner and the patient are able to adjust the frequencies for a desired comfort level and result. The output power, and time interval between pulsations are also fully adjustable with the use of potentiometers located on the control unit.

It will be appreciated by those of ordinary skill in the art that this invention is not limited to any one wave length, wave frequency or amplitude, but there are numerous combinations and sub-combinations which may be utilized within the contemplation of this invention.

Figure 12:
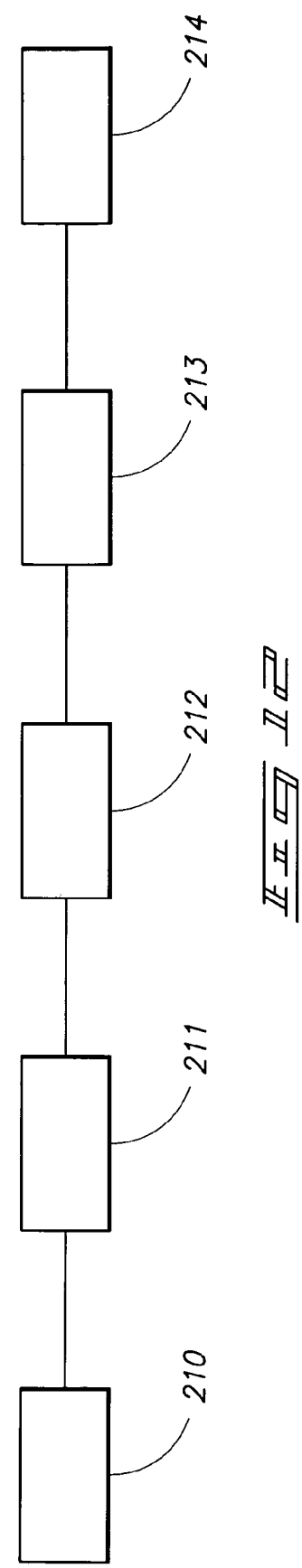
FIG. 12 is a block diagram representation of certain elements contemplated by embodiments of this invention.

FIG. 12 is a block diagram of one example of one embodiment contemplated by this invention, showing a programmable logic controller (PLC) 210, a high speed microprocessor (HSMP) 211, a digital-to-analog converter (DAC) 212 an amplifier 213 to provide the one or more waves which are pulsed or energized into the coil in the wave applicator 214, also sometimes referred to as a silicone module. The control unit provides, selects and controls any desired frequency or set of frequencies that are applied or energized to the coil windings. It will be appreciated by those of ordinary skill in the art that while these components are disclosed as exemplary, the invention may be practiced in numerous different ways with any one of a number of components utilized to deliver the desired waves and combination of waves, all within the contemplation of this invention.

Figure 13A:
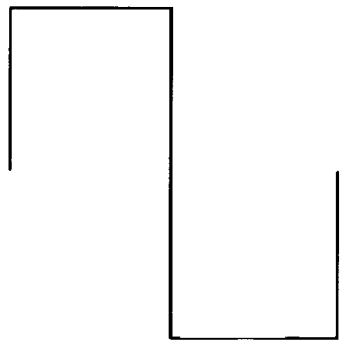
FIGS. 13A-D shows examples of wave generation using a high speed microprocessor and the effect of increasing the number of segments defining the wave in the microprocessor.
Figure 13B:
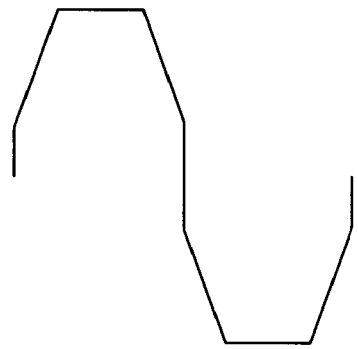
Figure 13C:
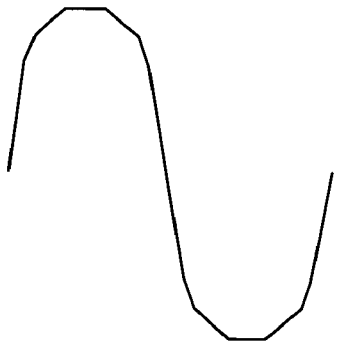
Figure 13D:
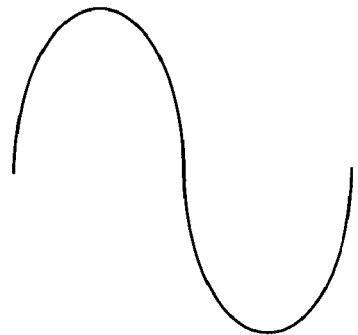

FIGS. 13A, 13B, 13C and 13D illustrate different sine wave generation techniques which may be utilized to generate waves by a high speed microprocessor. FIG. 13A shows a sine wave generated in four (4) segments, FIG. 13B shows a sine wave generated in nine (9), FIG. 13C illustrates a sine wave generated in thirty (30) segments, and FIG. 13D illustrates a sine wave generated in thirty thousand (30,000) segments. It is clear from the waves shown in FIG. 13D, that the sine wave generated in thirty thousand (30,000) segments appears to the human eye to be a perfect arcuate sinusoidal wave. It is by this sine wave generation technique, utilizing a microprocessor, that it is preferred that this multitude of frequencies shown or illustrated in FIG. 11 is generated concurrently, and then imparted on the target area to be healed or to receive therapy.

In some embodiments of this invention, all of the wave patterns are within the audio wave range. Coupling as many as 5 frequencies into one output can be used to treated scar tissue, pain and inflamation. A typical wave formation could be 100 hertz, 500 hertz, 1,000 hertz, 5,000 hertz, 10,000 hertz, and 20,000 hertz coupled into one output. Since the control unit is infinitely adjustable, both the practitioner and the patient are able to adjust the frequencies for a desired comfort level and result. The output power, and time interval between pulsations are also fully adjustable with the use of potentiometers located on the control unit.

As will be appreciated by those of reasonable skill in the art there are numerous embodiments to this invention, and variations of elements and components which may be used, all within the scope of this invention.

In one embodiment for example, a wave applicator for applying at least one wave to a mammal is provided, the wave applicator comprised of: a wave applicator framework; a silicone layer operatively connected to the wave applicator framework and configured for placement at or near the skin of a mammal; at least one magnet mounted relative to the framework, the at least one magnet having a cavity portion; an electrical coil movably mounted relative to the framework and positioned at least partially within the cavity portion of the at least one magnet; and wherein the electrical coil configured to receive at least one wave.

In further embodiments to those in the preceding paragraphs, a wave applicator may be provided: further wherein the silicone layer is molded and part of the wave applicator framework; further wherein at least a portion of the silicone layer is configured to vibrate in response to sound waves received from the electrical coil; further wherein the coil is movably mounted within the wave applicator framework; and further wherein the wave applicator framework also comprises a housing for the applicator; further wherein the magnet is positioned around and adjacent at least part of the coil; further wherein the magnet surrounds the coil; and further wherein the at least one wave is a sinusoidal wave; further wherein the at least one wave is a digital wave; further wherein the at least one wave includes a plurality of sinusoidal waves; wherein the at least one wave includes a first wave and a second wave and further wherein the first wave is different type of wave than the second wave; further wherein the at least one wave includes a first wave with a first wavelength and a second wave with a second wavelength, and further wherein the first wavelength is different than the second wavelength; further wherein at least a portion of the silicone layer is configured to vibrate in response to sound waves received from the electrical coil; and/or further wherein at least part of the silicone layer is at least semi-flexible such that it may vibrate in response to waves received from the electrical coil.

In another embodiment, a method for applying at least one wave to a mammal may be provided, comprising the following: providing a wave applicator; providing a silicone layer for placement at or near the skin of a mammal; and applying at least one wave to the silicone layer for a therapeutic affect on the mammal. This method may be further provided wherein the silicone layer is integral with the wave applicator.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A wave applicator for applying at least one wave to a mammal, the wave applicator comprised of:
   a wave applicator framework;
   a silicone layer operatively connected to the wave applicator framework and configured for placement at or near the skin of a mammal;
   at least one magnet mounted relative to the framework, the at least one magnet having a cavity portion;
   an electrical coil movably mounted relative to the framework and positioned at least partially within the cavity portion of the at least one magnet; and
   wherein the electrical coil is configured to receive at least one wave.

2. A wave applicator as recited in claim 1, and further wherein the silicone layer is molded and part of the wave applicator framework.

3. A wave applicator as recited in claim 2, and further wherein at least a portion of the silicone layer is configured to vibrate in response to sound waves received from the electrical coil.

4. A wave applicator as recited in claim 1, and further wherein the coil is movably mounted within the wave applicator framework.

5. A wave applicator as recited in claim 1, and further wherein the wave applicator framework also comprises a housing for the applicator.

6. A wave applicator as recited in claim 1, and further wherein the magnet is positioned around and adjacent at least part of the coil.

7. A wave applicator as recited in claim 1, and further wherein the magnet surrounds the coil.

8. A wave applicator as recited in claim 1, and further wherein the at least one wave is a sinusoidal wave.

9. A wave applicator as recited in claim 1, and further wherein the at least one wave is a digital wave.

10. A wave applicator as recited in claim 1, and further wherein the at least one wave includes a plurality of sinusoidal waves.

11. A wave applicator as recited in claim 1, and further wherein the at least one wave includes a first wave and a second wave, and further wherein the first wave is a different type of wave than the second wave.

12. A wave applicator as recited in claim 1, and further wherein the at least one wave includes a first wave with a first wavelength and a second wave with a second wavelength, and further wherein the first wavelength is different than the second wavelength.

13. A wave applicator as recited in claim 1, and further wherein at least a portion of the silicone layer is configured to vibrate in response to sound waves received from the electrical coil.

14. A wave applicator as recited in claim 1, and further wherein at least part of the silicone layer is at least semi-flexible such that it may vibrate in response to waves received from the electrical coil.

* * * * *